US006696481B2

(12) United States Patent
Damien et al.

(10) Patent No.: US 6,696,481 B2
(45) Date of Patent: Feb. 24, 2004

(54) SALT OF PERINDOPRIL AND PHARMACEUTICAL COMPOSITIONS CONTAINING IT

(75) Inventors: Gérard Damien, Orleans (FR); François Lefoulon, Orleans (FR); Bernard Marchand, Verneuil sur Seine (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 53 days.

(21) Appl. No.: 10/371,865

(22) Filed: Feb. 21, 2003

(65) Prior Publication Data

US 2003/0199568 A1 Oct. 23, 2003

(51) Int. Cl.[7] ..................... A61K 31/404; C07D 209/12

(52) U.S. Cl. ..................... 514/412; 514/419; 548/452; 548/492

(58) Field of Search ................. 514/412, 419; 548/452, 492

(56) References Cited

FOREIGN PATENT DOCUMENTS

EP          0049658      *  4/1982

* cited by examiner

Primary Examiner—Joseph K. McKane
Assistant Examiner—Sonya Wright
(74) Attorney, Agent, or Firm—The Firm of Hueschen and Sage

(57) ABSTRACT

The present invention relates to a new salt of perindopril and to pharmaceutical compositions containing it, and Medicaments for treatment of hypertension and heart failure.

5 Claims, No Drawings

SALT OF PERINDOPRIL AND PHARMACEUTICAL COMPOSITIONS CONTAINING IT

The present invention relates to a new salt of perindopril and to pharmaceutical compositions containing it. Perindopril, or (2S)-2-[(1S)-carbethoxybutylamino]-1-oxopropyl-(2S,3aS,7aS)perhydroindole-carboxylic acid, an angiotensin I converting enzyme inhibitor (CEI), is a compound known especially for the treatment of arterial hypertension and heart failure.

Perindopril has previously been described in the Patent Specification EP 0 049 658. In that European patent it is mentioned, as is usual, that the compounds of the invention may be presented in the form of addition salts with a pharmaceutically acceptable, mineral or organic, base or acid. The compounds described in that patent are in a non-salt form and primarily, when addition salts with a pharmaceutically acceptable base or acid are mentioned by way of example, the sodium salt or the maleate are given.

In the development of that product, however, it has proved very difficult to find a pharmaceutically acceptable salt having not only good bioavailability but also adequate stability to be suitable for the preparation and storage of pharmaceutical compositions.

In the studies originally carried out on the product, the tert-butylamine salt of perindopril proved to have adequate qualities for development of the product and it is this tert-butylamine salt of perindopril that is currently marketed.

The non-salt form has been studied, as well as the maleate and the sodium salt. In the course of temperature and humidity stability studies it was found that the sodium salt was not suitable for handling because it is immediately converted into an oil on contact with the atmosphere; as for the non-salt form and the maleate, they degrade rapidly under such conditions (approximately 25 to 30% of product degraded in 8 days at 50° C.).

The tert-butylamine salt was thus alone in exhibiting the best stability compared to the other forms studied. However, in view of the intrinsic fragility of perindopril, the tert-butylamine salt has not been capable of providing a complete solution to the problems of the product's stability to heat and humidity. Indeed, for marketing, tablets of perindopril tert-butylamine salt must, in certain countries, be protected with additional packaging measures. Moreover, even for temperate-climate countries, that instability has made it impossible to obtain a shelf-life of more than 2 years for the tablets. Finally, for marketing of the tablets, they have to be marked "to be stored at a temperature less than or equal to 30 degrees".

These constraints are, of course, onerous, especially in terms of organisation and cost, and it has appeared especially useful to try to develop a new perindopril salt in order to reduce the constraints due to the tert-butylamine salt.

Numerous salts were studied and, as indicated hereinbefore, the salts customarily used in the pharmaceutical sector proved to be unusable.

On the other hand, and in surprising manner, it has been found that the arginine salt of perindopril, besides being new, has entirely unexpected advantages over all the other salts studied and, more especially, over the tert-butylamine salt of perindopril.

The present invention accordingly relates to the arginine salt of perindopril, its hydrates and also to the pharmaceutical compositions comprising it.

The arginine salt of perindopril is preferentially the salt of natural arginine (L-arginine).

The pharmaceutical compositions according to the invention accordingly comprise the arginine salt of perindopril together with one or more, non-toxic, pharmaceutically acceptable and appropriate excipients.

Among the pharmaceutical compositions according to the invention there may be mentioned more especially those that are suitable for oral, parenteral or nasal administration, tablets or dragees, sublingual tablets, gelatin capsules, lozenges, suppositories, creams, ointments, dermal gels etc.

The pharmaceutical compositions according to the invention will preferably be immediate-release tablets.

The useful dosage varies according to the age and weight of the patient, the nature and severity of the disorder and also the administration route, which may be oral, nasal, rectal or parenteral.

The amount of the arginine salt contained in the compositions according to the invention is 0.2 to 10 mg, preferentially from 1 to 10 mg. These pharmaceutical compositions are of use in the treatment of hypertension and heart failure.

The basic characteristics of this salt are very great stability to heat and to humidity compared to the tert-butylamine salt.

Long-term stability studies carried out under very precise temperature and humidity conditions have yielded the results indicated in the Table hereinbelow.

In that study, perindopril was assayed by inverse-phase high-pressure liquid chromatography using, as eluant, an aqueous phase (comprising sodium heptane-sulphonate, and the pH of which is 2) and acetonitrile (67/33). Detection of the product was carried out by UV (215 nm).

The study was carried out using immediate-release tablets containing either 2.4 mg of the arginine salt of perindopril or 2.0 mg of the tert-butylamine salt of perindopril (each of the two tablets containing 1.7 mg of perindopril). The tablets were assayed 6 months after the start of storage of the tablets at different temperatures and different relative humidities (% R.H.).

The arginine salt used in this study is the L-arginine salt. It has been prepared according to a classical method of salification of organic chemistry.

| Conditions 6 months | tert-Butylamine salt of perindopril Percentage remaining (%) | Arginine salt of perindopril Percentage remaining (%) |
| --- | --- | --- |
| 25° C. 60% R.H. | 101.0 | 99.5 |
| 30° C. 60% R.H. | 94.4 | 98.1 |
| 40° C. 75% R.H. | 67.2 | 98.6 |

The results presented in the Table above show extremely clearly the very great stability of the arginine salt compared to the tert-butylamine salt. Indeed, after 6 months, practically no degradation of the arginine salt has taken place whereas the tert-butylamine salt exhibits a degradation rate of approximately 33%.

These results are entirely unexpected and could not have been deduced from, or suggested by, the teaching of the literature on this product.

The results allow us to consider less onerous constraints with respect to the packaging of the pharmaceutical compositions and also to obtain a shelf-life of at least three years for our pharmaceutical compositions.

We claim:

1. An arginine salt of perindopril and its hydrates.

2. A pharmaceutical composition comprising, as active ingredient, the arginine salt of perindopril and its hydrates, in combination with one or more pharmaceutically acceptable excipients.

3. The pharmaceutical composition of claim 2, which is presented in the form of an immediate-release tablet.

4. The pharmaceutical composition of claim 2, which contains from 0.2 to 10 mg of the arginine salt of perindopril.

5. A method for treating a living animal body afflicted with hypertension and heart failure comprising the step of administering to the living animal body an amount of the pharmaceutical composition of claim 2 which is effective for the alleviation of said disorder.

* * * * *